(12) United States Patent
Lam

(10) Patent No.: US 9,402,642 B2
(45) Date of Patent: Aug. 2, 2016

(54) TONGUE VACUUM CLEANER

(71) Applicant: Richard Lam, Kingwood, TX (US)

(72) Inventor: Richard Lam, Kingwood, TX (US)

(73) Assignee: Richard Lam, Humble, TX (US)

( * ) Notice: Subject to any disclaimer, the term of this patent is extended or adjusted under 35 U.S.C. 154(b) by 516 days.

(21) Appl. No.: 13/987,460

(22) Filed: Jul. 26, 2013

(65) Prior Publication Data
US 2015/0026917 A1    Jan. 29, 2015

(51) Int. Cl.
*A47L 5/24* (2006.01)
*A61C 17/06* (2006.01)
*A61C 17/14* (2006.01)
*A61B 17/24* (2006.01)

(52) U.S. Cl.
CPC ............ *A61B 17/244* (2013.01); *A47L 5/24* (2013.01); *A61C 17/043* (2013.01); *A61C 17/046* (2013.01)

(58) Field of Classification Search
CPC .. A61B 17/244; A61C 17/043; A61C 17/046; A47L 5/20; A47L 5/24; A47L 7/0014
USPC .............................. 15/344, 167.1; 433/91, 92
See application file for complete search history.

(56) References Cited

U.S. PATENT DOCUMENTS

| 6,918,764 B2 * | 7/2005 | Ito ...................... A61C 17/0208 433/91 |
| 2005/0050676 A1* | 3/2005 | Khan ................... A61B 17/244 15/344 |
| 2005/0066996 A1* | 3/2005 | France .................. A64B 9/028 134/6 |

FOREIGN PATENT DOCUMENTS

JP    53135761 A    * 11/1978

* cited by examiner

*Primary Examiner* — Bryan R Muller

(57) ABSTRACT

A portable hand held tongue vacuum cleaner that includes a small vacuum pump and power supply contained within a hollow housing. A removable cleaning head is attached to a vacuum port which extends out from the housing. The cleaning head includes bristles and a centrally located vacuum tube whose end terminates just below the height of the bristles. The cleaning head is oriented at a forty-five degree angle with respect to the cleaning head extension tube. A removable filter trap is located inside the extension tube to catch debris removed from the surface of the tongue.

5 Claims, 8 Drawing Sheets

TONGUE VACUUM CLEANER

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of tongue cleaning devices and more specifically to portable tongue vacuum cleaner.

It is a known fact that the human tongue can be a breeding ground for bacteria that may prove to be harmful to an individual if not removed periodically. Methods for removing bacteria from the tongue include brushing, scraping and mouthwash. However, all these techniques can still leave bacterial debris on the tongue because the tongue's surface is like a miniature deep pile carpet, and some debris remain in the deeper crevices of the tongue's surface. In dental offices, some dentists take advantage of the availability of a vacuum system normally used for removing liquid from a person's mouth, and add a vacuum scraping tool to the vacuum tube to scrape clean the patient's tongue.

Sajid Khan in his patent application 2005/0050676 describes a hand held tongue vacuum cleaner. Although Kahn describes the basic concept of using a vacuum to clean the tongue, the specific details of the device's construction and use have not been delineated in either drawing form or written form and therefore make it very difficult to imagine a device that can be reduced to practice. For example Kahn talks about dirty matter passing through into a detachable waste chamber, but does not say how or where this occurs. Additionally, there is talk of a filter to allow clean air to pass into an exhaust port but also does not show how or where this acutely occurs. Finally, there is no discussion of the shape, angle or surface characteristics of the cleaning head. Therefore, although the idea of a portable vacuum cleaner for a tongue has been shown in the prior application sited, the specific and novel mechanism for the ideal execution of this idea has not been previously described or illustrated.

BRIEF SUMMARY OF THE INVENTION

The primary object of the invention is to provide a portable hand held device for cleaning a person's tongue.

Another object of the invention is to provide a tongue cleaning device that uses a vacuum and bristles to help remove debris from the tongue.

Another object of the invention is to provide a tongue cleaning device that uses an angled removable cleaning head that includes bristles, a central vacuum aperture and a filter trap for trapping debris as it is sucked from the surface of the tongue.

A further object of the invention is to provide a tongue cleaning device that securely holds and locks the cleaning head in the correct orientation for use until the user removes the head.

Yet another object of the invention is to provide a tongue cleaning device that is water resistant and can be recharged by an induction type charger.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed tongue vacuum cleaner comprising: a hollow housing, a diaphragm type vacuum pump, a pump connection tube, a pair of O rings, a motor, an on-off switch, a cleaning head, a cleaning head extension tube, a filter trap, an extension tube retaining assembly, a battery power supply, a recharging station, said vacuum pump, motor, switch and battery contained within said hollow housing, said on-off switch mounted on the front surface of said housing just below said cleaning head extension tube, said battery powering said motor, said motor powering said vacuum pump, said pump connection tube fixedly attached to said vacuum pump and extending outwardly in a perpendicular fashion from the upper portion of said housing, said O rings surrounding said pump connection tube, said cleaning head including a flat rigid plate having a plurality of bristles extending there-from and having a central tubular aperture extending to just below the height of said bristles, said cleaning head fixedly attached to said cleaning head extension tube, said cleaning head extension tube capable of being slidably inserted or removed over said pump connection tube and said O rings, said filter trap removably retained within said cleaning head extension tube between said cleaning head and the end of said pump connection tube, said extension tube retaining assembly attached to the outside of said housing and engaging in a spring biased manner at least one detent located on the outside wall of said cleaning head extension tube, and the base of said housing capable of being inserted into a recharging station for recharging said battery power supply.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
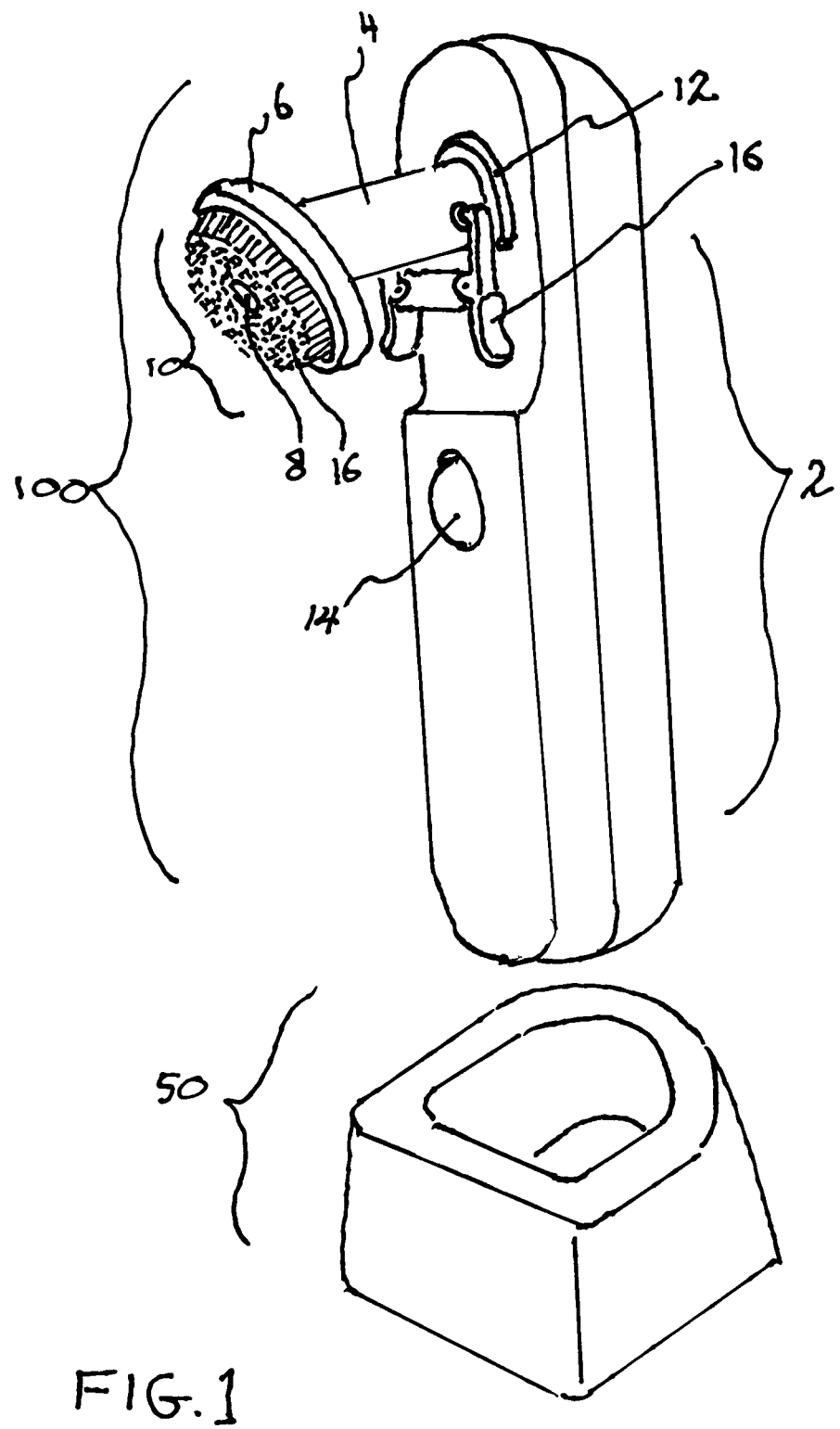
FIG. 1 is a perspective view of the portable tongue cleaner and recharging station of the present invention.
Figure 2:
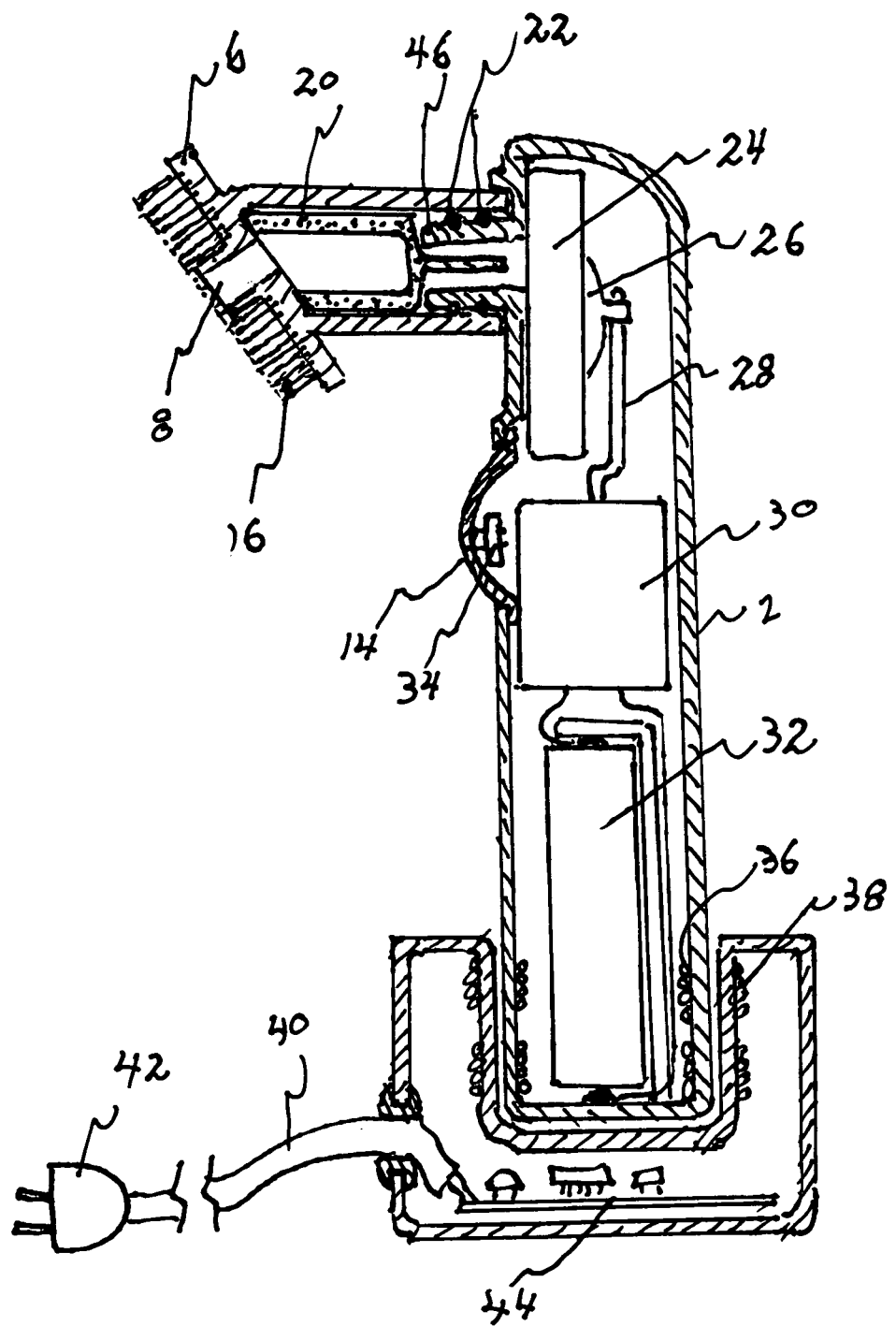
FIG. 2 is a side section view that bisects the invention.
Figure 6:
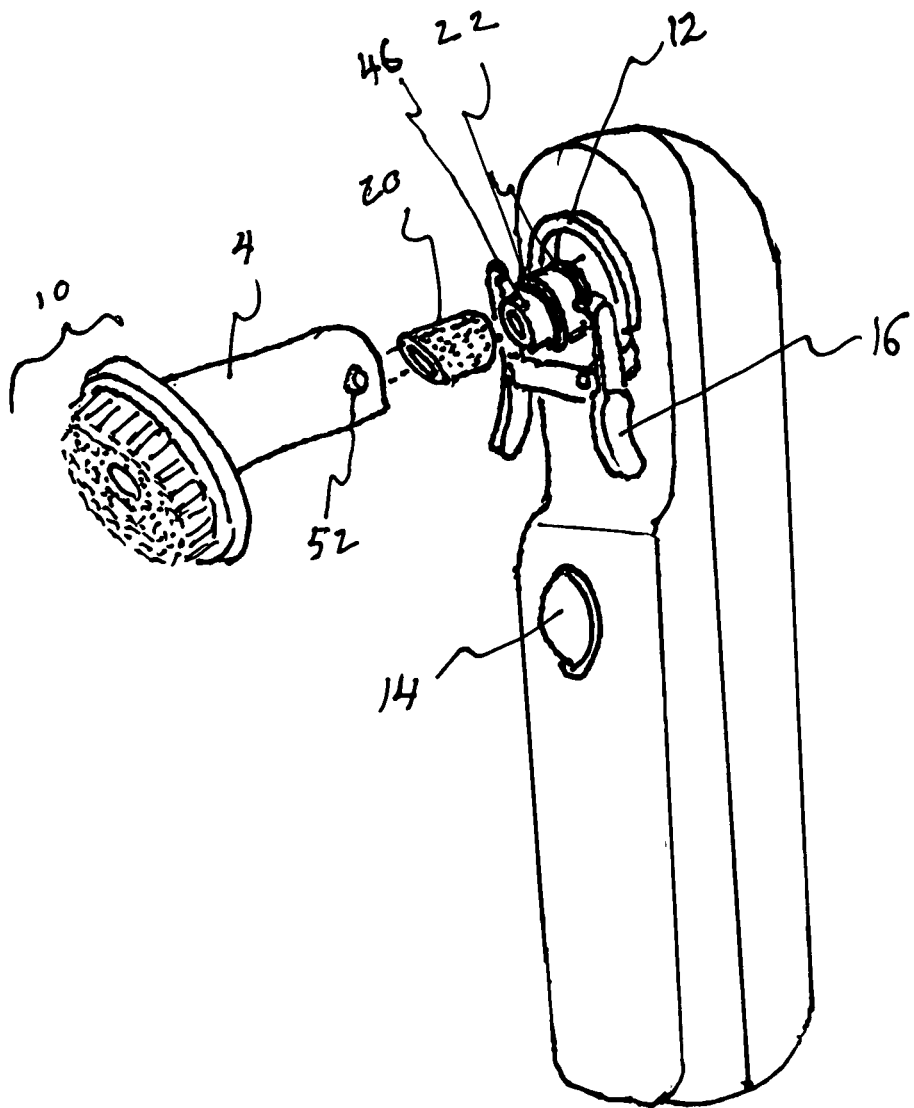
FIG. 6 is an exploded view of the invention.

Referring now to FIG. 1 we see a perspective view of the tongue cleaner 100 of the present invention and a recharging stand 50. A hollow housing 2 contains a pump 24 and motor 30 as will be explained in FIG. 2. An on off button 14 is placed at the front of the housing 2 so that it can be easily turned on by a user's thumb while holding the main body 2 in his or her hand. A cleaning head 10 is attached to a cleaning head extension tube 4 which has been slid onto a pump extension tube 46 as shown in FIGS. 2 and 6. A retaining assembly 16 helps lock the extension tube 4 to the rest of the main body during use.

The cleaning head 10 includes a rigid flat plate 6 that has a plurality of bristles 16 emanating from it. The bristles are all approximately one quarter of an inch tall. A central vacuum tube tip 8 is centrally fixed onto plate 6 and extends out to almost the same length as the bristles. The entire cleaning head 10 is angled at approximately a forty-five degree angle with respect to the cleaning head extension tube 4. This is an ideal ergonomic angle for the intended function of holding housing 2 in ones hand and brushing ones tongue with bristles 16. In operation, the bristles 16 tend to dislodge debris from the carpet-like surface of the tongue while the vacuum tip 8 sucks the loosened debris into the extension tube 4. Housing 2 base 3 can be inserted into a receptacle 5 in recharging station 50 to so that the batteries 32 inside the housing 2 can be recharged. The side section view FIG. 2 shows one of two batteries that are placed side by side in the housing 10.

Figure 4:
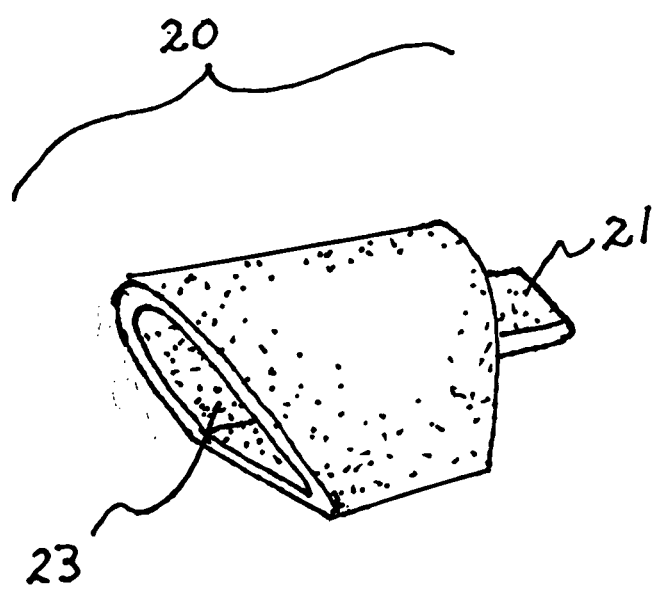
FIG. 4 is a perspective view of the filter trap.

FIG. 2 shows a section view that bisects the invention 100. Inside housing 2 is a battery power supply 32, a DC motor 30 and a diaphragm type vacuum pump 24. An offset shaft 28 causes the diaphragm 26 to pulse in and out creating a vacuum that causes suction into pump extension tube 46. Cleaning head extension tube 4 is slide over pump extension tube 46 and associated O rings 22 that fit in grooves in the tube 46 creating an air tight seal. A filter trap 20 is located between the tip of extension tube 46 and the rear of plate 6 and can catch debris that are sucked into the trap 20 during use. The filter trap is shaped to match the inside wall of extension tube 4 as shown in FIG. 4. The filter trap 20 is made of expanded polyethylene and has a trade name of Porex. The air holes in the walls of the trap 20 are large enough to let air through, but small enough to not let liquids or debris through. The filter 20 includes a pull tab 21 to make it easy for the user to remove the filter trap 20 after use. The unique location and construction of the filter trap 20 is important because it eliminates the requirement for a separate debris holding chamber and helps retain the air tight requirements of the entire assembly 100 because the filter 20 is trapped within the extension tube 4 so that O rings 22 are the only air tight seal needed in the assembly 100 other than the standard seals located in the vacuum pump 24.

After each use, the user can remove the cleaning head assembly 10, 4 and pull out the filter trap 20 by pull tab 21, and then clean the filter trap 20 under running water before returning it to the extension tube 4 making it ready for the next use. Optionally, the entire cleaning head 10, 5 and filter 20 can be discarded after each use.

Coils 36 inside the bottom area of housing 2 interact with induction coils 38 and associated electronics 44 in the recharging station 50 to recharge batteries 32. This type of recharging system allows the housing 2 to remain water resistant because no apertures are needed within the housing to gain access to metal connectors. The recharging stand is powered by standard 110VAC electricity from plug 42 and cord 40.

Figure 3:
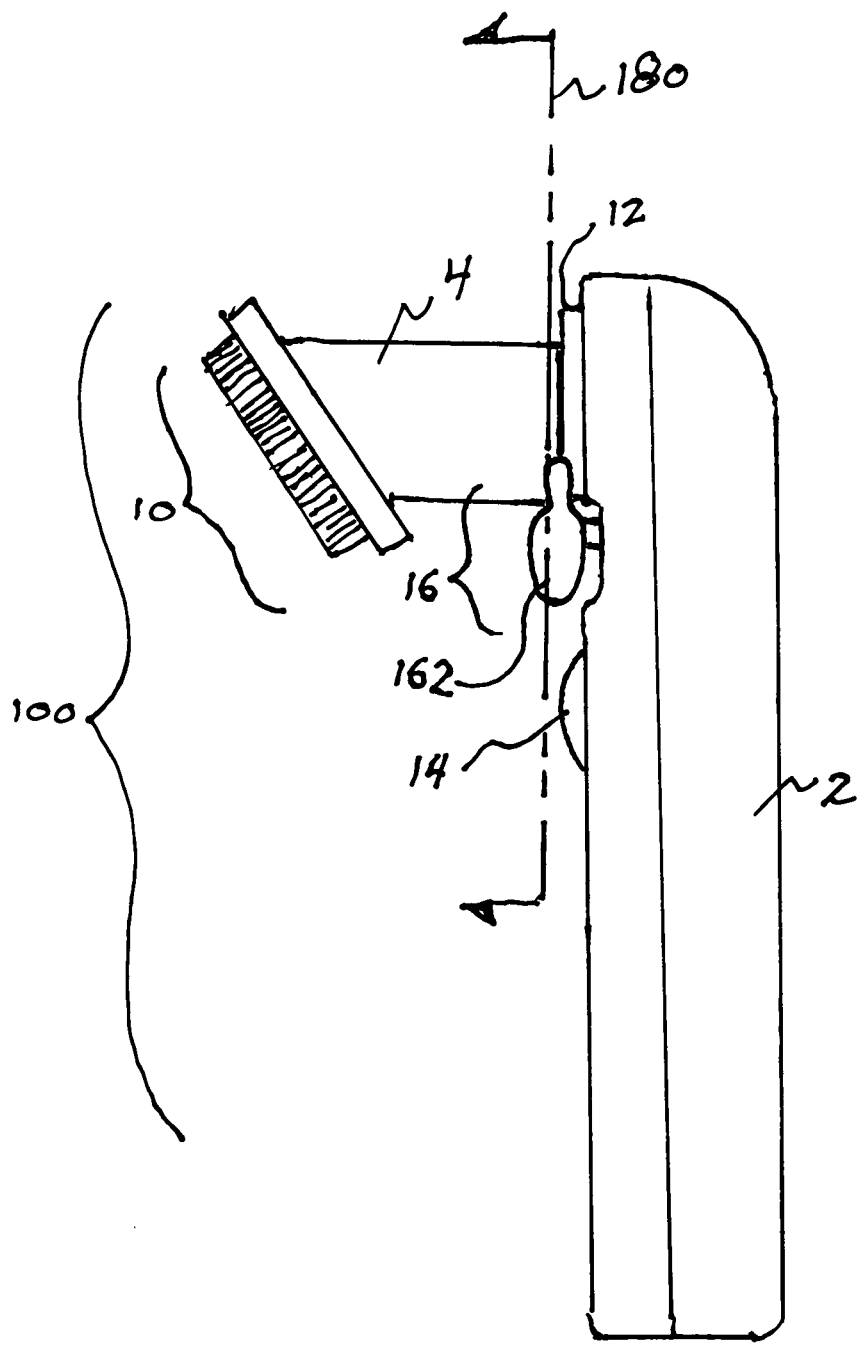
FIG. 3 is a side view of the invention.
Figure 5:
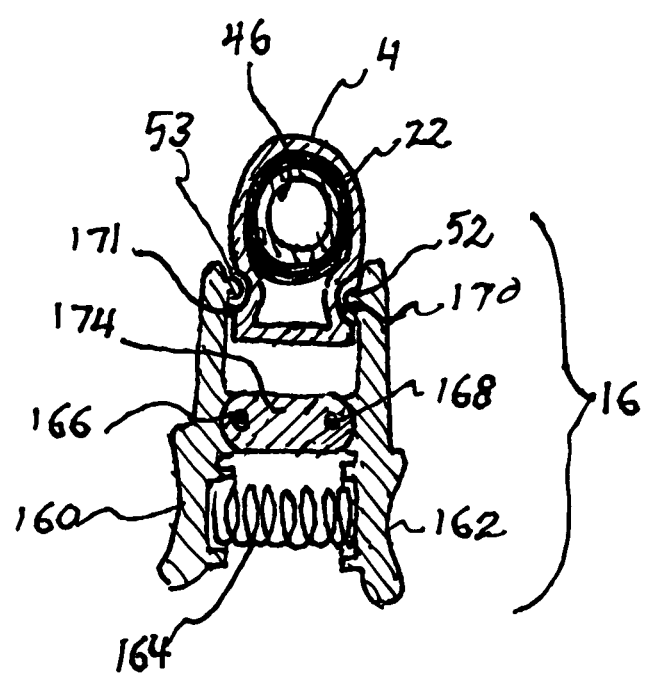
FIG. 5 is a front section view of the extension tube and tube retaining assembly.

FIG. 3 shows a side view of the invention 100. The diameter of housing 2 is approximately one and one half inches which is the ideal diameter for grasping in one's hand. One of the retaining members of retaining assembly 16 can be clearly seen. FIG. 5 shows a section view as defined by section line 180 in FIG. 3. FIG. 5 shows the tips 52, 53 of spring biased tabs 168, 166 engaged with detents 170, 171 in the side walls of pump extension tube 46. The tabs 168, 166 are hinge pinned 166, 158 to an extension arm 174 off the main body 2. A compression spring 164 spans the distance between the two tabs 160, 162 to provide inward force to tips 52, 53. To remove the extension tube 4 and attached cleaning head 10, the user presses the two tabs 160, 162 between his or her thumb and fore finger thereby releasing tips 52, 53 from detents 170, 171.

FIG. 6 shows an exploded view of the invention. Detent 52 can be clearly seen, as well as filter trap 20 as it is ready to be installed into extension tube 4. O rings 22 are clearly seen surrounding the pump extension tube 46.

Figure 7:
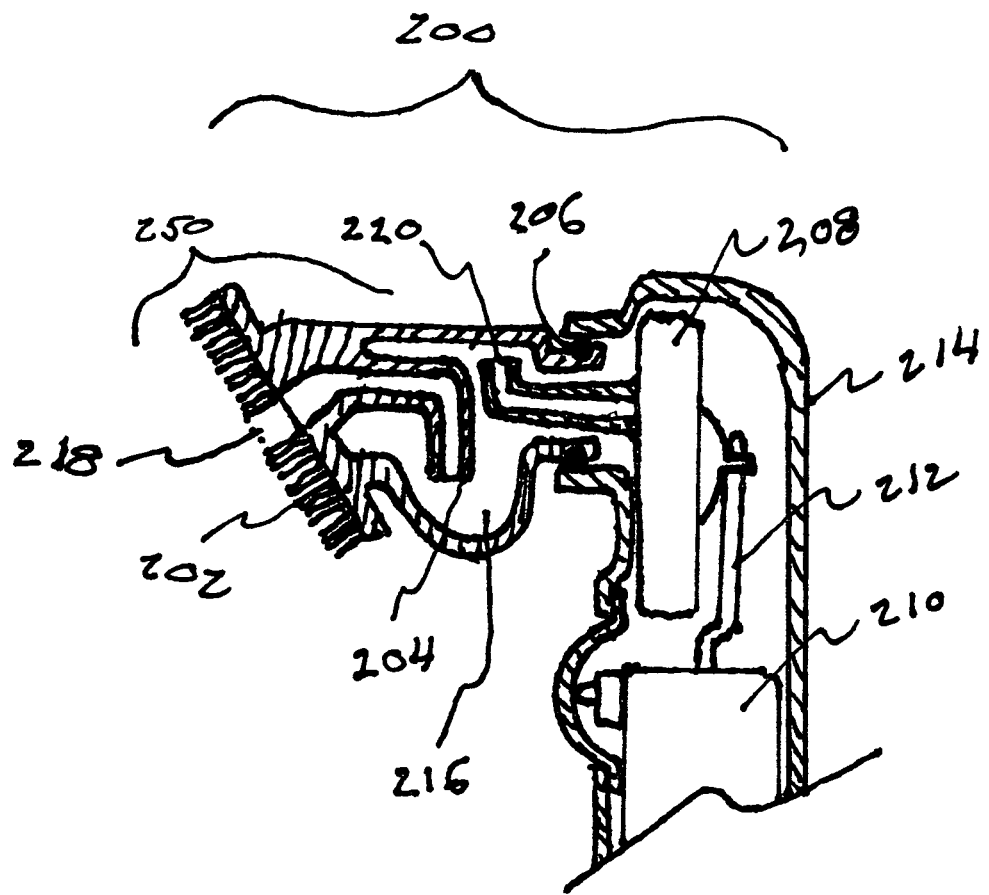
FIG. 7 is a partial side section view of an alternate embodiment of the invention.

FIG. 7 is a partial side section view of the invention 200 where in place of the air filter 20, a saliva reservoir 261 can catch excess saliva that is drawn in through opening 218 and directed downward by L shaped tube 204. The vacuum pump 208 terminates in an upwardly directed L shaped suction port tube 220. O ring 206 creates a vacuum retaining seal between removable head 250 and main body 214. The upward orientation of tube 220 and the downward orientation of tube 204 helps insure that the saliva that is drawn into the reservoir 216 does not accidentally enter vacuum suction port tube 220. Pump motor 210 and diaphragm pump member 208 operate in the same manner as described in the first embodiment. Tongue bristles 202 also operate in the same manner as described in the first embodiment.

Figure 8:
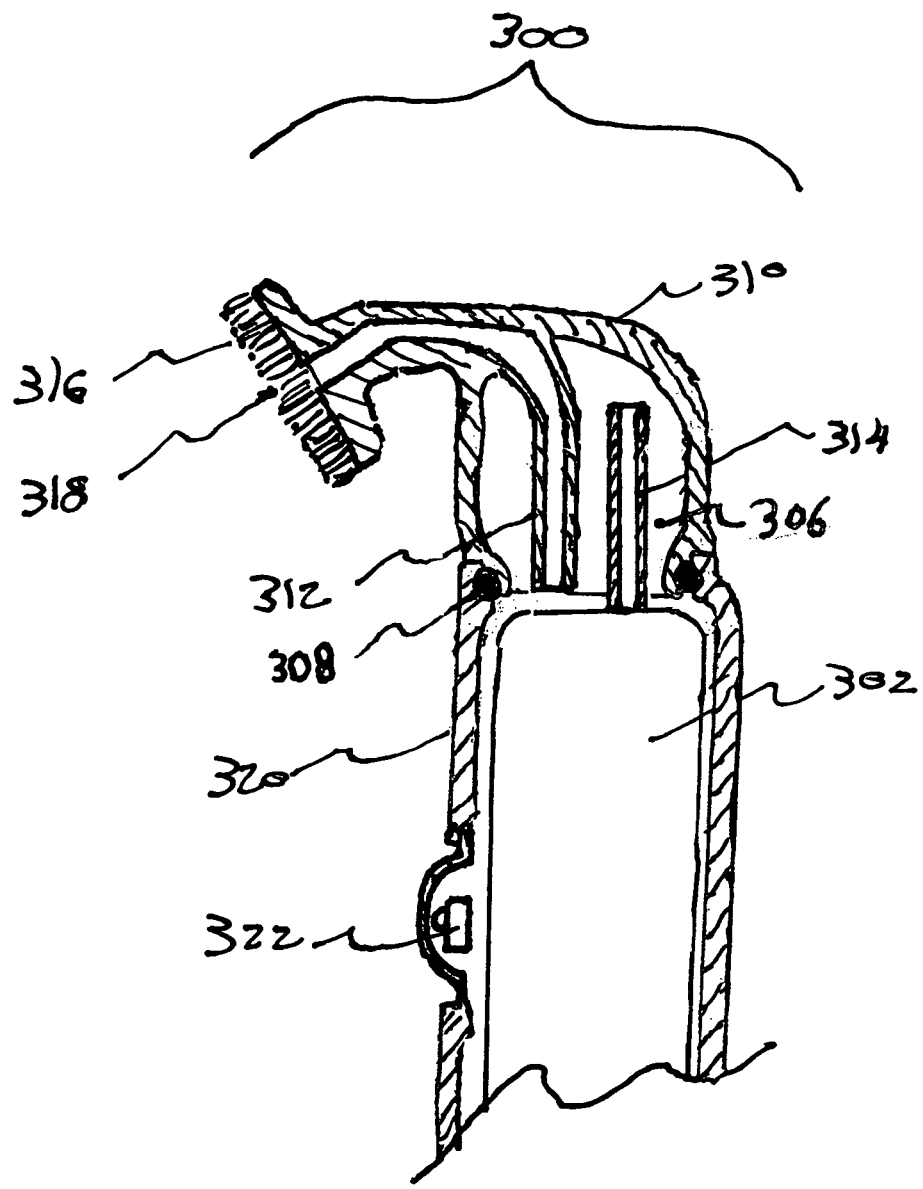
FIG. 8 is a partial side section view of a second alternate embodiment of the invention.

FIG. 8 is a partial side section view of a second embodiment of the invention 300 which is similar in concept to the version shown in FIG. 7 except that The vacuum tube 314 coming from pump and motor area 302 is in a vertical position, as is the saliva exit tube 312 coming from brush head 316 as it enters the brush head at central aperture 318. The head body 310 is removable from the main body 320 and is made air tight by gasket 308. When the user applies the tool 300, any excess saliva and or debris is sucked into area 306. The saliva is precluded from entering upwardly disposed vacuum tube 314 because tube 314 terminates at a much higher position than downwardly disposed saliva vacuum tube 312. Push button 322 operates in the same fashion as the main embodiment.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A tongue vacuum cleaner comprising:
a hollow housing;
a diaphragm type vacuum pump;
a pump connection tube;
a pair of O rings;
a motor;
an on-off switch;
a cleaning head;
a cleaning head extension tube;
a filter trap;

an extension tube retaining assembly;
a battery power supply;
a recharging station;
said vacuum pump, motor, switch and battery contained within said hollow housing;
said on-off switch mounted on the front surface of said housing just below said cleaning head extension tube
said battery powering said motor;
said motor powering said vacuum pump;
said pump connection tube fixedly attached to said vacuum pump and extending outwardly in a perpendicular fashion from the upper portion of said housing;
said O rings surrounding said pump connection tube;
said cleaning head including a flat rigid plate having a plurality of bristles extending there-from and having a central tubular aperture extending to just below the height of said bristles;
said cleaning head fixedly attached to said cleaning head extension tube;
said cleaning head extension tube extending out from said housing;
said cleaning head extension tube capable of being slidably inserted or removed over said pump connection tube and said O rings;
said filter trap removably retained within said cleaning head extension tube between said cleaning head and the end of said pump connection tube;
said extension tube retaining assembly attached to the outside of said housing and engaging in a spring biased manner at least one detent located on the outside wall of said cleaning head extension tube; and
the base of said housing capable of being inserted into a recharging station for recharging said battery power supply.

2. A tongue vacuum cleaner as claimed in claim 1 wherein said cleaning head is fixed at approximately a forty-five degree angle with relation to said cleaning head extension tube.

3. A tongue vacuum cleaner as claimed in claim 1 wherein said cleaning head extension tube has a D shaped cross section and plugs into a D shaped collar fixed to the outside of said housing.

4. A tongue vacuum cleaner as claimed in claim 1 wherein said recharging station includes induction charging coils mounted in the interior of said charging station that interact with coils mounted within the base portion of said hollow housing.

5. A tongue vacuum cleaner as claimed in claim 1 wherein said filter trap includes a pull tab located at its distal end to allow a user to pull out said filter trap with his or her fingers.

* * * * *